United States Patent [19]
Howard, III

[11] Patent Number: 5,800,535
[45] Date of Patent: *Sep. 1, 1998

[54] WIRELESS PROSTHETIC ELECTRODE FOR THE BRAIN

[75] Inventor: Matthew A. Howard, III, Iowa City, Iowa

[73] Assignee: The University of Iowa Research Foundation, Iowa City, Iowa

[*] Notice: The term of this patent shall not extend beyond the expiration date of Pat. No. 5,496,369.

[21] Appl. No.: 332,757

[22] Filed: Nov. 1, 1994

Related U.S. Application Data

[63] Continuation-in-part of Ser. No. 194,017, Feb. 9, 1994, Pat. No. 5,496,369.
[51] Int. Cl.$^6$ .................................................. A61F 2/18
[52] U.S. Cl. .................................................. 623/10; 623/66
[58] Field of Search ........................ 600/25; 607/2, 607/55–57; 623/10–11, 24, 66

[56] References Cited

U.S. PATENT DOCUMENTS

| | | | |
|---|---|---|---|
| 4,357,497 | 11/1982 | Hochmair et al. | 607/57 |
| 4,969,468 | 11/1990 | Byers et al. | 607/118 |
| 5,000,194 | 3/1991 | Honert et al. | |
| 5,271,397 | 12/1993 | Seligman et al. | |
| 5,496,369 | 3/1996 | Howard, III | 623/10 |

FOREIGN PATENT DOCUMENTS

| | | | |
|---|---|---|---|
| 0259906 | 3/1988 | European Pat. Off. | |

OTHER PUBLICATIONS

Center for Integrated Sensors and Circuits, *Passive Multichannel Recording and Stimulating Electrode Arrays: A Catalog of Available Designs*, (Jul., 1991).

Cohen et al., A Prospective, Randomized Study of Cochlear Implants, *N.E.J. of Med.* 328 (4):233–237, (Jan., 1993).

Dobelle et al., A Prosthesis for the Deaf Based on Cortical Stimulation, *Ann. Otol.* 82:445–463, (1973).

Dobelle et al., Artificial Vision for the Blind: Electrical Stimulation of Visual Cortex Offers Hope for a Functional Prosthethis, *Science* 183:440–444 (1974).

Eisenberg et al., Electrical Stimulation of the Auditory Brain Stem Structure in Deafened Adults, *J. Rehab. Research* 24 (3):9–22 (1987).

Medtronic, *The ITREL® II. The third generation of excellence*, (1991).

Morgan, The First Reported Case of Electrical Stimulation of the Human Brain, J. Hist. Med., pp. 51–63 (Jan., 1982).

Penfield et al., Somatic Motor and Sensory Representation in the Cerebral Cortex of Man as Studied by Electrical Stimulation, *Brain* 60:389–443 (1937).

Penfield et al., The Brain's Record of Auditory and Visual Experience, *Brain* 86:596–696 (1963).

Walker, The Development of the Concept of Cerebral Localization in the Nineteenth Century, *Bulletin His. Med.* 31 (2):99–121 (Mar.–Apr., 1957).

Eggermont, "Neural Interaction In Cat Primary Auditory Cortex," Oct. 1992; pp. 1216–1228, Journal of Neurophysiology vol. 68 No. 4.

*Primary Examiner*—Robert A. Clarke
*Attorney, Agent, or Firm*—Fleshner & Kim

[57] ABSTRACT

A wireless neural prosthetic device for a primary auditory cortex of a patient includes either a speech processor or a stimulating device for receiving and processing information and a wireless electrode arranged in the primary auditory cortex having a plurality of electrical contacts. The electrode can be arranged in the patient's primary auditory cortex and each of the plurality of electrical contacts independently outputs electrical discharges in accordance with the processed electrical signals. The plurality of electrical contacts can be arranged to approximately tonotopically match the primary auditory cortex.

22 Claims, 10 Drawing Sheets

WIRELESS PROSTHETIC ELECTRODE FOR THE BRAIN

This application is a continuation-in-part of U.S. patent application Ser. No. 08/194,017 filed Feb. 9, 1994, now U.S. Pat. No. 5,496,369, the contents of which are incorporated herein by reference.

BACKGROUND OF THE INVENTION

1. Field of the Invention

This invention relates generally to a wireless apparatus and method for providing an electrode with electrical contacts which remain localized with respect to specified neurons or groups of neurons.

The apparatus and method can be used to treat a hard-of-hearing or deaf patient whose hearing cannot be restored with a cochlear implant, and this embodiment of the invention relates, in particular, to a wireless human cerebral cortex neural prosthetic for delivering electrical signals to the patient's primary auditory cortex.

The apparatus and method can also be used to treat tinnitus, and, this embodiment of the invention relates, in particular, to a wireless human cerebral cortex neural prosthetic for delivering geometrically dispersed electrical signals to the patient's primary auditory cortex or the patient's thalamus.

2. Background of the Related Art

Prior to the nineteenth century, physicians and scientists believed the brain was an organ with functional properties distributed equally through its mass. Localization of specific functions within subregions of the brain was first demonstrated in the 1800s, and provided the fundamental conceptual framework for all of modern neuroscience and neurosurgery. As it became clear that brain subregions served specific functions such as movement of the extremities, and touch sensation, it was also noted that direct electrical stimulation of the surface of these brain regions could cause partial reproduction of these functions. Morgan, J. P., "The first reported case of electrical stimulation of the human brain," *J. History of Medicine*, January 1982:51–63, 1982; Walker, A. E., "The development of the concept of cerebral localization in the nineteenth century," *Bull. Hist. Med.*, 31:99–121, 1957.

The most extensive work on electrical stimulation "mapping" of the human brain surface was carried out over several decades by Dr. Wilder Penfield, a neurosurgeon and physiologist at the Montreal Neurological Institute, mostly during the early to mid-1900s. He made precise observations during cortical stimulation of hundreds of awake patients undergoing brain surgery for intractable epilepsy. Among his many findings, he noted that stimulation of the visual and hearing areas of the brain reproducibly caused the patients to experience visual and auditory phenomena. Penfield, W. et al., "Somatic motor and sensory representation in the cerebral cortex of man as studied by electrical stimulation," *Brain* 60:389–443, 1937; Penfield, W. et al., *Epilepsy and the Functional Anatomy of the Human Brain*, London:Churchill, 1954; Penfield, W. et al., "The brain's record of auditory and visual experience," *Brain*, 86:595–696, 1963. Following the results of early human brain mapping studies, electrical stimulation of sensory brain regions to restore lost function was a logical therapeutic extrapolation. Drs. Brindley and Lewin of the University of Cambridge were the first to reduce the concept to practice by implanting a patient with a visual cortex neural prosthetic device. Brindley, G. S. et al., "The sensations produced by electrical stimulation of the visual cortex," *J. Physiol.* 196:479–493, 1968. Their device consisted of an array of thin, flat electrodes placed on the surface of the visual cortex. The electrodes were remotely controlled with radio signals. A similar system was later tested at the University of Utah by Dr. Dobelle and colleagues. Dobelle, W. H. et al., "Artificial vision for the blind: stimulation of the visual cortex offers hope for a functional prosthesis," *Science* 183:440–444, 1974.

Findings from these early British and American studies were consistent. Patients reliably perceived flashes of light (phosphenes) during periods of electrical stimulation, and simple patterns of phosphenes could be generated by simultaneously activating multiple contacts. While these findings strongly suggested the eventual feasibility of a cortical visual prosthetic device, many important design problems were insurmountable at that time.

Among these were an inability to precisely stimulate very small volumes of brain, the requirement for high stimulation currents to induce phosphenes, and an inability to access the patient's full "visual space" with the large array of surface electrodes used. Additionally, there were no miniature video cameras and small, powerful computers at the time capable of converting visual images into complex electrical stimulation sequences at ultra high speed.

The University of Utah has discontinued visual cortex prostheses research. However, the concept has been pursued at NIP where significant additional advances have been made. Their most important discovery to date relates to the use of needle shaped penetrating depth electrodes instead of flat surface stimulating electrodes. Bak, M., et al., "Visual sensations produced by intracortical microstimulation of the human occipital cortex," *Med. Biol. Eng. Comput.*, 28:257–259, 1990. Penetrating electrodes represent a major design improvement. They are placed within the brain tissue itself so there is optimal surface contact with elements of the brain that are targeted for stimulation. As a result, patients perceive visual phosphenes with approximately a thousand-fold less stimulation current than that required when surface electrodes are used. This allows for safe, chronic stimulation of very small discreet volumes of brain.

Additionally, penetrating electrodes transform what was in the past a two dimensional implant-brain interface (flat disks on the surface of the brain) into a three dimensional interface (multiple needle-like electrodes in parallel extending from the surface into the brain substance), which vastly increases the device's access to stimulation targets below the surface. To use a television screen analogy, a two dimensional surface-electrode array may have the potential of generating an image on the "screen" composed of approximately one hundred discreet dots ("pixels"), whereas a three-dimensional array would potentially generate an image with many thousands of dots. The huge potential increase in image resolution would be achieved using a small fraction of the stimulation currents used in the past.

Penetrating electrodes have the potential to markedly increase both image quality and the safety of the stimulation process. Human experimental studies continue at the NIH campus. Extramural NIH funding is also directed at supporting engineering research on penetrating electrodes optimally suited for neural prosthetics applications. The University of Michigan, for example, has made use of computer-chip manufacturing techniques to synthesize exquisitely small electrode arrays. The etched electrical contacts on these devices are so small that the distance separating adjacent contacts can be in the range of 50 micrometers, approximately the diameter of two nerve cell bodies. Drake, K. L. et al., "Performance of planar multisite microprobes in recording extracellular single-unit intracortical activity," *IEEE Trans. BME*, 35:719–732, 1988.

During the 1970s the neural prosthetics group at the University of Utah not only explored the feasibility of a visual cortex neural prosthetic device, but carried out experiments in auditory cortex stimulation as well. Led by Dr. Dobelle, they formed a mobile research group that traveled to surgical centers throughout the United States when suitable experimental subjects were identified. These were patients who required temporal lobe surgery for tumor removal or treatment of intractable epilepsy, and who agreed to participate in the experimental protocol. Dobelle, W. H. et al., "A prosthesis for the deaf based on cortical stimulation," *Ann. Otol*, 82:445–463, 1973.

The primary auditory region of the human brain is buried deep within the Sylvian fissure. It is not visible from the brain surface and its exact location varies slightly from one person to the next. MRI and CT scanners were not invented at the time of Dr. Dobelle's experiments so the anatomy of the patients' auditory cortex could not be studied prior to surgery, and this region could only be visualized with difficulty in the operating room after the Sylvian fissure was surgically dissected. Once the buried auditory cortex was exposed, surface stimulating electrodes were placed by hand over the area thought to be auditory cortex and the brain was stimulated in a fashion similar to that used to generate visual phosphenes.

Reproducible sound sensations were generated in the experimental subjects. Though these preliminary findings were encouraging, a range of limitations precluded further work by this group. Among the more daunting problems the Utah group faced were recruiting suitable patients for the experimental study and obtaining good stimulation characteristics from the experimental surface electrodes. The minimal stimulation threshold for eliciting sound sensations was found to be 6 milliamperes, which is too high to be tolerated chronically and is thousands of times greater than currents found subsequently to be required to generate phosphenes in visual cortex using penetrating electrodes.

Recent advances in MRI and computer technology now allow detailed preoperative imaging of human auditory cortex.

Another major technical innovation developed since the time of Dr. Dobelle's early experiments is the cochlear implant. An important aspect of the cochlear implant technology, which is now highly refined, involves transducing sound into complex electrical stimulation sequences. This large body of technical knowledge developed over the last twenty years will be directly applicable to the auditory cortex prosthetic device and aid immeasurably in its research and development.

Normal Hearing

Mechanisms of human hearing are reviewed briefly to provide a framework for discussion of auditory neural prosthetic devices. The auditory system is composed of many structural components that are connected extensively by bundles of nerve fibers. The system's overall function is to enable humans to extract usable information from sounds in the environment. By transducing acoustic signals into electrical signals that can then be processed in the brain, humans are able to discriminate amongst a wide range of sounds with great precision.

Figure 1A:
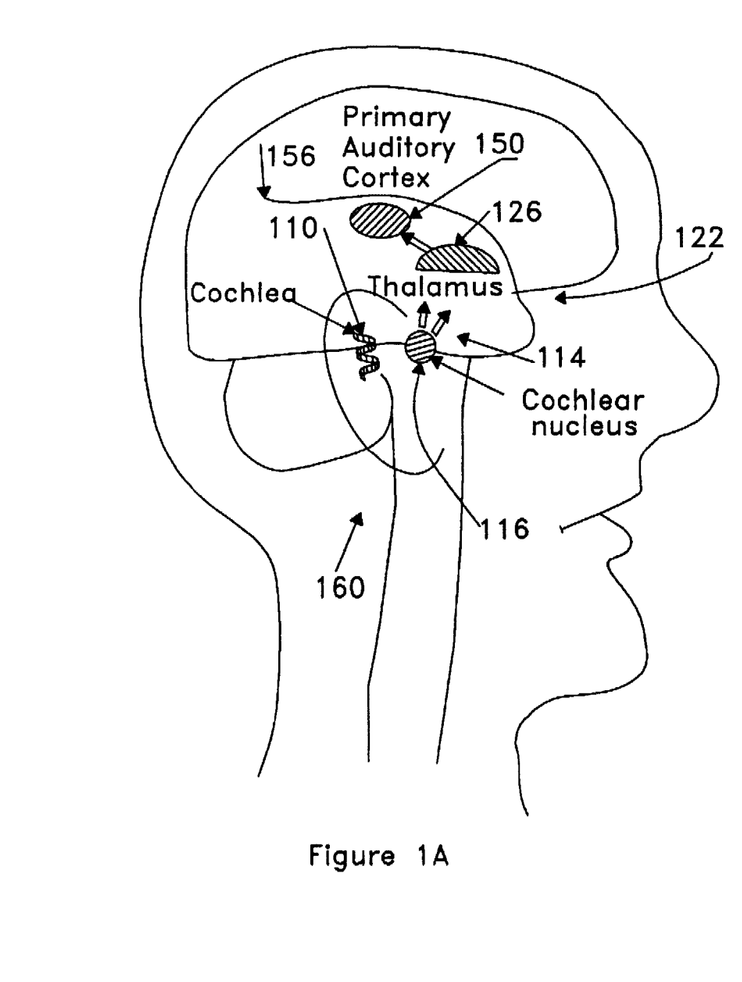
FIGS. 1A and 1B show the orientation of a patient's primary auditory cortex in relation to the patient's cochlea and cochlear nucleus.
Figure 1B:
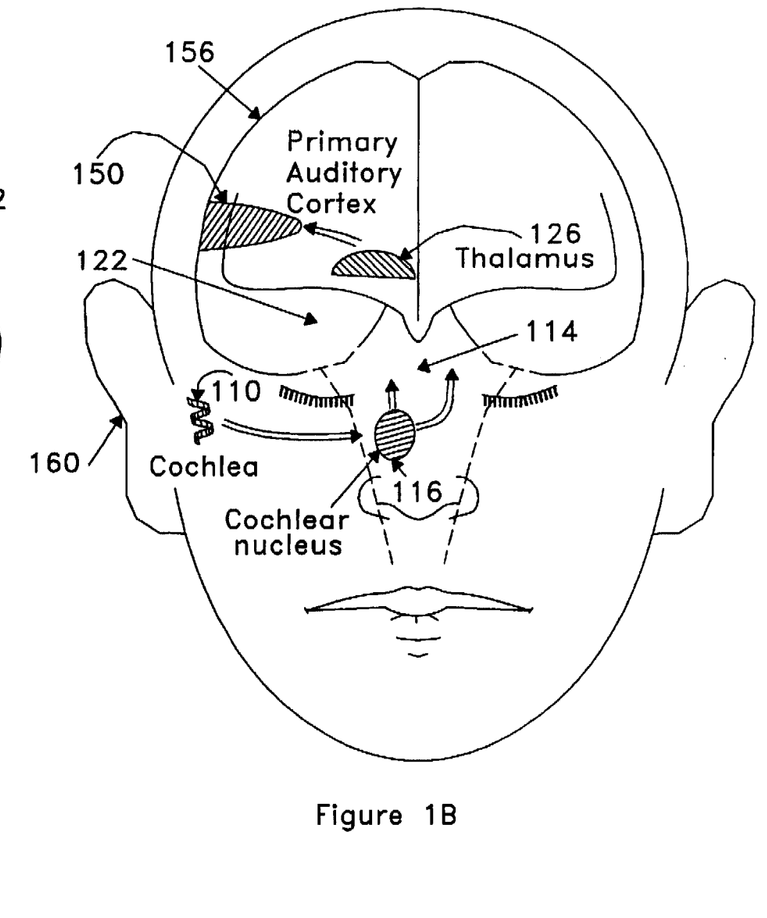

FIGS. 1A and 1B show a side and front view of areas involved in the hearing process. In particular, the normal transduction of sound waves into electrical signals occurs in cochlea 110, a part of the inner ear located within temporal bone (not shown). Cochlea 110 is tonotopically organized, meaning different parts of cochlea 110 respond optimally to different tones; one end of cochlea 110 responds best to high frequency tones, while the other end responds best to low frequency tones. Cochlea 110 converts the tones to electrical signals which are then received by cochlea nucleus 116. This converted information is passed from cochlea 110 into brain stem 114 by way of electrical signals carried along the acoustic nerve and in particular, cranial nerve VIII (not shown).

The next important auditory structure encountered is cochlear nucleus 116 in the brain stem 114. As the acoustic nerve leaves the temporal bone and enters skull cavity 122, it penetrates brain stem 114 and relays coded signals to cochlear nucleus 116, which is also tonotopically organized. Through many fiber-tract interconnections and relays (not shown), sound signals are analyzed at sites throughout brain stem 114 and thalamus 126. The final signal analysis site is auditory cortex 150 situated in temporal lobe 156.

The mechanisms of function of these various structures has also been extensively studied. The function of cochlea 110 is the most well-understood and the function of auditory cortex 150 is the least understood. For example, removal of the cochlea 110 results in complete deafness in ear 160, whereas removal of auditory cortex 150 from one side produces minimal deficits. Despite extensive neural connections with other components of the auditory system, auditory cortex 150 does not appear to be necessary for many auditory functions.

Cochlear Implant

Cochlear implants were designed for patients who are deaf as a result of loss of the cochlea's sound transduction mechanism. Implant candidates must have an intact acoustic nerve capable of carrying electrical signals away from the middle ear into the brain stem. The device converts sound waves into electrical signals which are delivered through a multi-contact stimulating electrode. The stimulating electrode is surgically inserted by an otolaryngologist into the damaged cochlea. Activation of the contacts stimulates acoustic nerve terminals which would normally be activated by the cochlear sound transduction mechanism. The patient perceives sound as the coded electrical signal is carried from the middle ear into the brain by the acoustic nerve. Cohen, N. L. et al., "A prospective, randomized study of cochlear implants," *N. Engl. J. Med.*, 328:233–7, 1993.

In patients with hearing loss caused by dysfunction at the level of the cochlea, cochlear implants can be remarkably effective in restoring hearing. For example, some previously deaf patients are able to understand conversations over the telephone following insertion of a cochlear implant.

Cochlear implants are surgically placed in the middle ear which is situated in the temporal bone. In patients who are already deaf, there is very little chance of any additional injury being caused by placement of a cochlear implant; they are very safe devices. Because of the low health risk associated with placing cochlear implants, obtaining experimental subjects during the early development stage was not difficult. In this setting design improvements occurred rapidly.

Cochlear Nucleus Implant

Patients are not candidates for cochlear implants if their hearing loss results from damage in auditory regions other than the cochlea. Because the first auditory relay station "downstream" from the cochlea and auditory nerve is the brainstem cochlear nucleus, this structure is a logical candidate for consideration as an implantation site. This approach was first developed at the House Ear Institute. Eisenberg, L. S. et al., "Electrical stimulation of the auditory brainstem structure in deafened adults," *J. Rehab. Res.* 24:9–22, 1987; Hitselberger, W. E. et al., "Cochlear nucleus implant," *Otolaryngol. Head Neck Surg.*, 92:52–54, 1984. As is the case with cochlear implants, sound waves are translated into a complex electrical code F. The implant's stimulation terminals are placed up against the cochlear nucleus, and the patient perceives sounds when the system is activated.

Data on efficacy is limited because relatively few patients have been tested with this device. Early findings demonstrate, however, that some degree of useful hearing is restored using this device. Environmental sounds such as a knock at the door and a telephone ringing have been detected by patients with a cochlear nucleus implant, and this improved auditory function has increased patients' ability to live independently.

Although work in the visual cortex demonstrates that central nervous system penetrating electrodes are significantly more effective than surface electrodes, use of penetrating electrodes in the cochlear nucleus has been discontinued for safety reasons described below.

For several reasons, there is significantly more risk associated with cochlear nucleus implants than cochlear implants. The cochlear nucleus is situated in the brain stem; a very sensitive and vital structure. Neurosurgical procedures in the brain stem are among the most difficult and dangerous operations performed. Infiltrating tumors within the substance of the brainstem, for example, are usually considered surgically inoperable. Surgical manipulation or injury of brainstem elements can cause devastating complications, including loss of normal swallowing functions, loss of control of eye movements, paralysis, coma, and death.

Because of their internationally renowned acoustic neuroma practice, doctors at the House Ear Institute are among the most experienced surgeons in the world at gaining surgical access to the brainstem surface. Acoustic neuromas are tumors arising from the supporting cells of the acoustic nerve. As they enlarge, these tumors expand into the cranial cavity and press up against the brainstem. Patients typically present with hearing loss, and a number of surgical approaches have been developed by otolaryngologists and neurosurgeons to remove these lesions.

Surgeons at the House Ear Institute have played a pioneering role in acoustic neuroma surgery and now routinely perform operations where the tumor is safely removed and the brainstem surface is visualized. They have placed cochlear nucleus implants in deaf patients who have lost function of both acoustic nerves and are undergoing removal of an acoustic neuroma. This affords access to the brainstem surface during a medically necessary procedure.

The first cochlear nucleus implant used penetrating electrodes. These functioned well initially, however within two months they had migrated further into the brainstem, causing tingling sensation in the patient's hip as adjacent fiber tracts were inadvertently stimulated. This system was removed and surface electrodes have been used for cochlear nucleus implants since that time. Risks of implanting a cochlear nucleus device are such that patients are only candidates for implantation if they require surgery in that area of the brainstem for some other, usually life threatening reason.

It is difficult to find suitable patients for implantation and testing of cochlear nucleus implants. The most likely candidates are patients who have a rare form of neurofibromatosis and acoustic neuromas on both acoustic nerves. Martuza, R. L. et al., "Neurofibromatosis 2 (Bilateral Acoustic Neurofibromatosis)," *N. Engl. J. Med.*, 318:684–688, 1988. A small number of these patients are referred regularly to such institutions as the House Ear Institute. Many university medical centers, however, would be unable to identify a single suitable candidate during a full year. In the fourteen years since its initial clinical application at the House Ear Institute, cochlear nucleus implant use and testing has remained quite restricted (less than two implants per year average during the epoch reported in Eisenberg, L. S. et al., "Electrical stimulation of the auditory brainstem structure in deafened adults," *J. Rehab. Res.* 24:9–22, 1987.

Treating Deafness

Devices designed to treat deafness must take into consideration the underlying cause of deafness. For example, a patient with defective cochlea 110 who still has a functional acoustic nerve, may benefit from an artificial cochlea (cochlear implant). However, if the acoustic nerve is damaged and cannot carry electrical signals, then the problem is "too far downstream" in the signal processing sequence for a cochlear implant to be effective. In that situation, artificial signals must enter the auditory system "beyond the block" either in brain stem 114 or in auditory cortex 150.

Tinnitus Treatment

Tinnitus is a disorder where a patient experiences a sound sensation within the head ("a ringing in the ears") in absence of an external stimulus. This uncontrollable ringing can be extremely uncomfortable and often results in severe disability. Tinnitus is a very common disorder affecting an estimated 15% of the U.S. population according to the National Institutes for Health, 1989 National Strategic Research Plan. Hence, approximately 9 million Americans have clinically significant tinnitus with 2 million of those being severely disabled by the disorder.

There are no treatments currently available that consistently eliminate tinnitus although many different types of treatments have been attempted. This wide variety of attempted treatments attests to the unsatisfactory state of current tinnitus therapy. Several more common attempts will be discussed below.

One approach involves suppression of abnormal neural activity within the auditory nervous system with various anticonvulsant medications. Examples of such anticonvulsant medications include Xylocaine and Lidocaine which are administered intravenously. In addition, since the clinical impact of tinnitus is significantly influenced by the patient's psychological state, antidepressants, sedatives, biofeedback and counseling methods are also used. None of these methods has been shown to be consistently effective.

Another widely used approach to treating tinnitus involves "masking" undesirable sound perception by presenting alternative sounds to the patient using an external sound generator. In particular, an external sound generator is attached to the patient's ear (similar to a hearing aid) and the generator outputs sounds into the patient's ear. Although this approach has met with moderate success, it has several significant drawbacks. First, such an approach requires that the patient not be deaf in the ear which uses the external sound generator. That is, the external sound generator cannot effectively mask sounds to a deaf ear which subsequently developed tinnitus. Second, the external sound generator can be inconvenient to use and can actually result in loss of hearing acuity in healthy ears.

Yet another approach involves surgical resection of the auditory nerve itself. This more dangerous approach is usually only attempted if the patient suffers form large acoustic neuromas and tinnitus. In this situation, the auditory nerve is not resected for the specific purpose of eliminating tinnitus but is removed as an almost inevitable complication of large tumor removal. In a wide series of patients with tinnitus who underwent this surgical procedure of acoustic nerve resection, only 40% were improved, 10% were improved and 50% were actually worse.

An alternative and somewhat more successful approach involves electrical stimulation of the cochlea. In patients who have tinnitus and have received a cochlear implant, as many as half reported improvement in their tinnitus after implantation. Round window stimulation has also been useful in improving tinnitus in selected patients. However, the success rate of this approach has also remained relatively low.

SUMMARY OF THE INVENTION

It is therefore an object of the invention to provide a wireless prosthetic which can be placed in a cerebral cortex to reconstitute sensor input to the brain using microstimulation.

Another object of the invention is to provide a wireless prosthetic which can be positioned in the brain such that an entire range of tonal frequencies processed by the human brain are accessed thereby.

Another object of the invention is to provide a wireless prosthetic which allows a physician to physiologically test location and function of neural prosthetic electrodes in patients undergoing surgery for medically intractable epilepsy.

Another object of the invention to provide a wireless prosthetic apparatus which can be placed in one of a patient's cerebral cortex or in the patient's thalamus to reduce the effects of tinnitus.

Another object of the invention is to provide a wireless prosthetic apparatus which can be positioned in the brain such that electric discharges can be accurately delivered to geometrically dispersed locations in either the cortex or thalamus.

Another object of the invention is to provide a wireless prosthetic which allows a physician to physiologically test location and function of neural prosthetic electrodes to reduce or eliminate the patient's tinnitus.

One advantage of the invention is that it does not require wires to electrically couple the electrode to the stimulator or processor.

Another advantage of the invention is that it includes contacts which enable a deaf patient to hear even though the patient's problem is not in his or her cochlear regions but instead is farther "down stream."

Another advantage of the invention is that it can utilize a single electrode.

Another advantage of the invention is that it penetrates the brain thus requiring significantly less current to stimulate localized areas of the auditory cortex.

Another advantage of the invention is that the contacts are sufficiently closely arranged next to each other to provide high resolution stimulation of the auditory cortex.

Another advantage of the invention is that it can be used to reduce or eliminate the effects of tinnitus.

Another advantage of the invention is that it can utilize a single electrode.

Another advantage of the invention is that it penetrates the brain thus requiring significantly less current to stimulate localized areas of the cortex or the thalamus.

Another advantage of the invention is that the contacts are sufficiently closely arranged next to each other to provide high geometric resolution stimulation of the auditory cortex.

One feature of the invention is that it includes a wireless penetrating longitudinal support or electrode.

Another feature of the invention is that it includes multiple contacts on the longitudinal support.

Another feature of the invention is that it includes a speech processor.

Another feature of the invention is that each contact can separately introduce electrical discharges in the primary auditory cortex.

Another feature of the invention is that it can include a stimulation device.

Another feature of the invention is that each contact can separately introduce electrical discharges in the primary auditory cortex.

These and other objects, advantages and features are accomplished by the provision of a wireless neural prosthetic device for a brain target zone of a patient, for receiving processed electrical signals from an exterior device, including: an electrode arranged in the brain target zone having a plurality of electrical contacts; and circuitry electrically coupled to the plurality of electrical contacts for receiving the processed electrical signals and selectively outputting electrical discharges to the plurality of electrical contacts in accordance with the processed electrical signals.

These and other objects, advantages and features are also accomplished by the provision of a method of inserting the wireless neural prosthetic device including the steps of: attaching a stereotaxic introducer probe onto the attachment end; inserting the electrode into the brain target zone; inputting one of a gas, a liquid and a malleable solid material into the attachment end of the electrode; and detaching the probe from the attachment end of the electrode.

These and other objects, advantages and features are also accomplished by the provision of a wireless neural prosthetic system for a targeted brain zone of a patient, including: a processor for outputting processed electrical signals; an electrode arranged in the targeted brain zone having a plurality of electrical contacts, the electrode being arranged in the targeted brain zone and each of the plurality of electrical contacts outputting electrical discharges in accordance with the processed electrical signals; and circuitry, electrically coupled to the plurality of electrical contacts, for receiving the processed electrical signals and outputting electrical discharges to the plurality of electrical contacts in accordance with the processed electrical signals.

These and other objects, advantages and features are also accomplished by the provision of a neural prosthetic apparatus for a primary auditory cortex of a patient, comprising: a speech processor for receiving and processing audio information and for outputting processed electrical signals; an electrode arranged in the primary auditory cortex having a plurality of electrical contacts, the electrode being arranged in the primary auditory cortex and each of the plurality of electrical contacts outputting electrical discharges in accordance with the processed electrical signals; and circuitry electrically coupled to the plurality of electrical contacts for receiving the processed electrical signals and outputting electrical discharges to the plurality of electrical contacts in accordance with the processed electrical signals.

These and other objects, advantages and features of the present invention will become more apparent from the following description of embodiments thereof taken in conjunction with the accompanying drawings.

DETAILED DESCRIPTION OF THE PREFERRED EMBODIMENTS

Advanced imaging combined with an intraoperative stereotactic system now enable placement of penetrating electrodes into auditory cortex during routine epilepsy surgery without dissection of the Sylvian fissure.

Primary auditory cortex 150 in FIGS. 1A and 1B is tonotopically organized, meaning stimulation in different areas is likely to cause the patient to perceive different tones. These tones form the building blocks of complex sound phenomena such as speech. Tonotopic organization is a fundamental characteristic of the cochlea and cochlear nucleus as well, as discussed above. Auditory cortex 150, however, has its tonotopic map stretched across a larger volume of tissue (greater that twice the volume of cochlear nucleus 116). Greater tissue volume enables placement of a greater number of electrical contacts for a given tonotopic zone. This results in increased signal resolution and improved clarity of auditory sensation. Finally, because of anatomical differences, auditory cortex 150 can accommodate penetrating electrode arrays which cannot be safely placed into the cochlear nucleus.

Figure 2A:
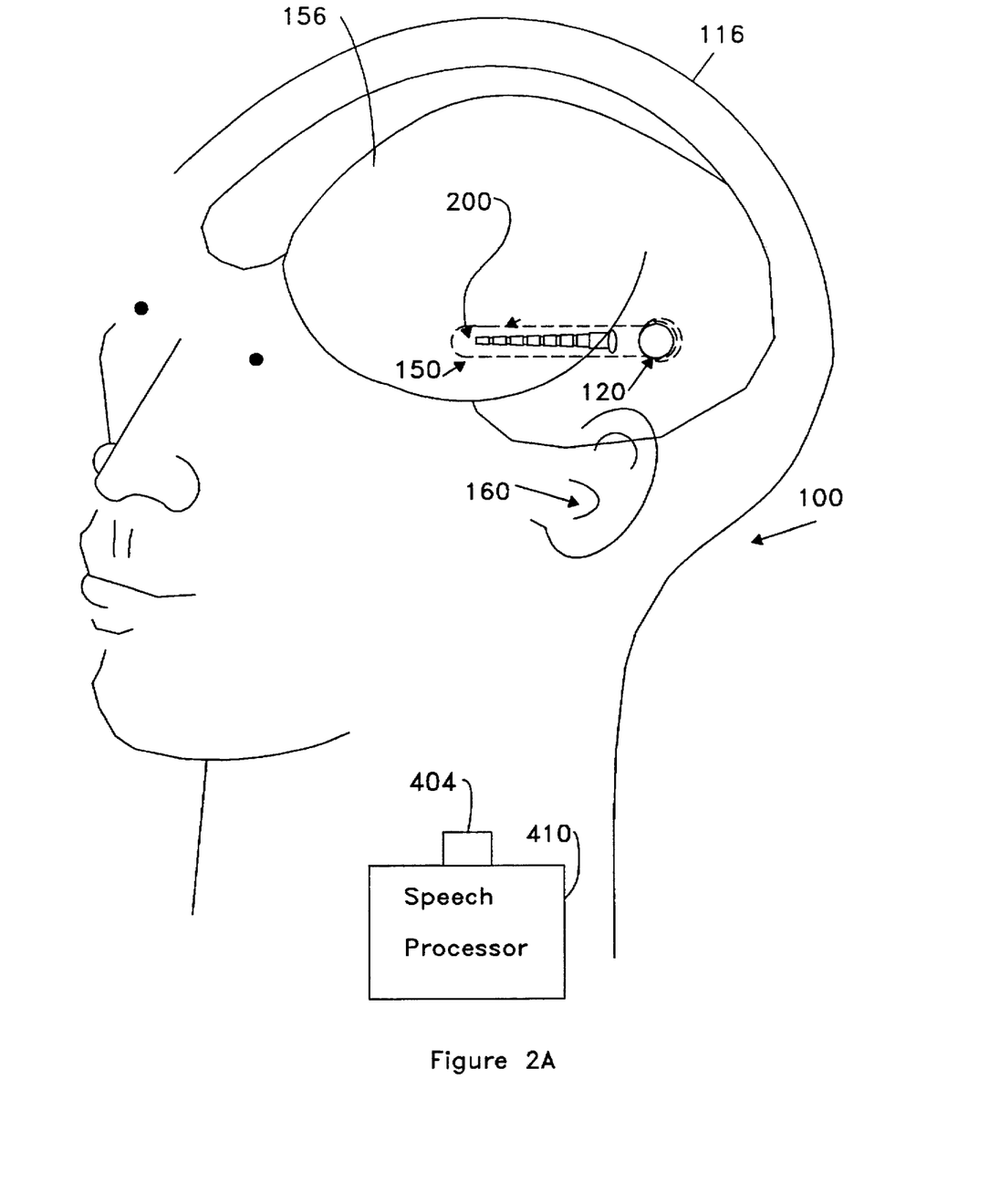
FIG. 2A shows a wireless human cerebral cortex neural prosthetic system according to one embodiment of the invention.
Figures 2B, 2C:
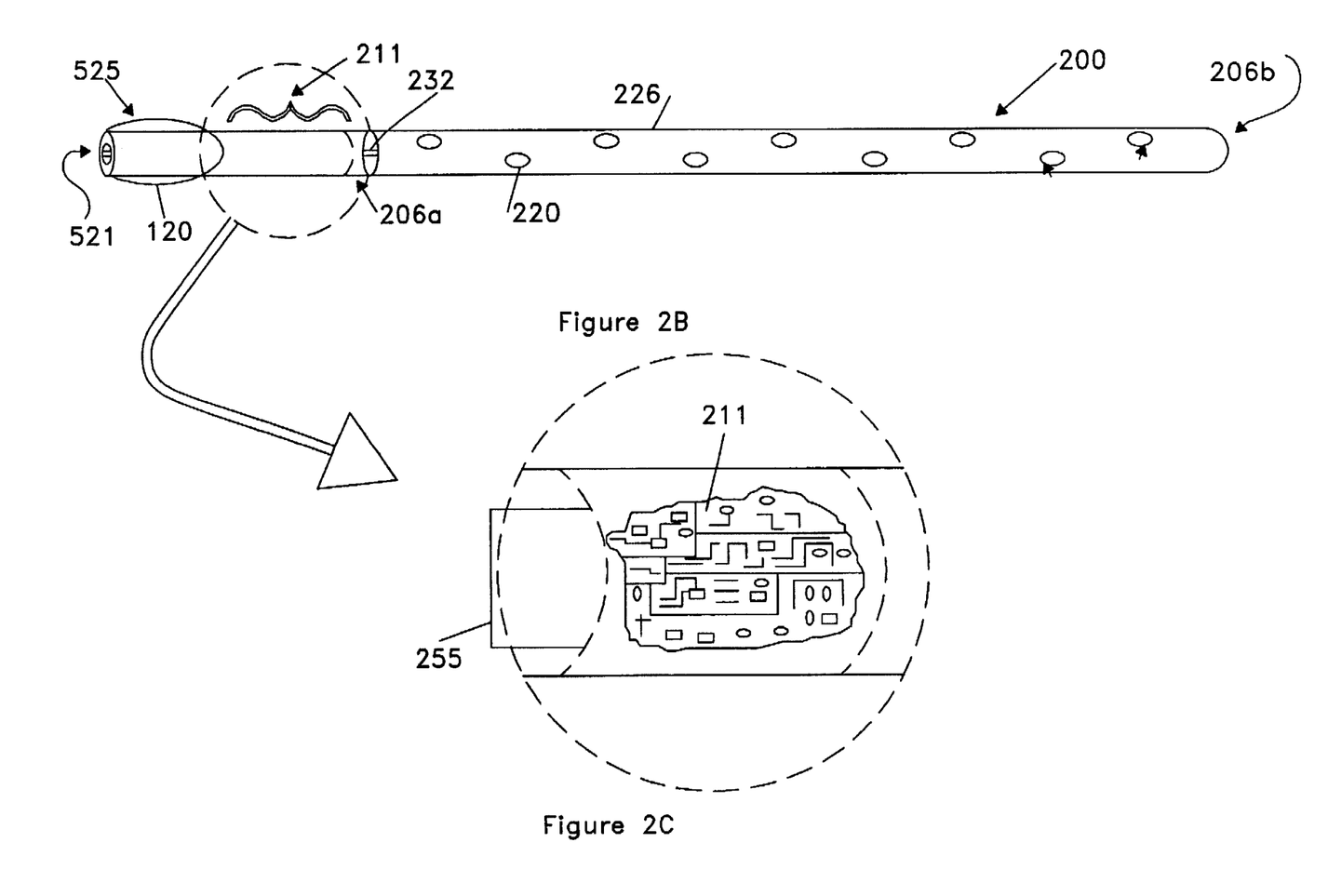
FIG. 2B shows a wireless human cerebral cortex neural prosthetic electrode (support) according to one embodiment of the invention.
FIG. 2C shows a closeup of the transmission and receiving electronics in the electrode.

FIG. 2A shows a wireless human cerebral cortex neural prosthetic 200 according to one embodiment of the invention. FIGS. 2B and 2C show closer views of prosthetic 200 and a portion of prosthetic 200 containing microchip circuitry 211 which transmits and receives signals to and from a speech processor 410 via a transmitter/receiver unit 404.

Transmitter/receiver unit 404 need not be mechanically secured to processor 410, it only needs to be electrically connected via wires (not shown) to processor 410. Transmitter/receiver unit 404 acts as a transmitter and receiver of the electromagnetic waves as discussed below. Prosthetic 200 has a first end 206a for attachment and a second end 206b for penetration which is blunt or smoothly curved. Prosthetic 200 has electrical contacts 220 along a longitudinal support 226. Support 226 may be a rigid or flexible elongate rod or wire, which may be substantially cylindrical in shape, and can be anywhere from several millimeters long to several centimeters long. Electrical contacts 220 are small metal pads which can be separately electrically charged via respective wires 232 which couple contacts 220 to microchip circuitry 211. Electrical contacts 220 may be arranged as a three-dimensional array on support 226, and are spaced approximately 10 micrometers to several millimeters apart and preferably approximately 50 to 150 micrometers apart.

Speech processor 410 outputs magnetic or electromagnetic signals (referred to here as processor signals) via transmitter/receiver unit 404 and these processor signals are received by circuitry 211 which in turn demodulates and/or decodes these processor signals to determine which contacts 220 on prosthetic 200 will be charged to stimulate neurons in cortex 150. In this case, unit 404 acts as a transmitter, transmitting the processor signals and circuitry 211 acts as a receiver, receiving, and demodulating/decoding the processor signals to determine which contacts to charge. Similarly, contacts 220 can act as conductive sensors, sensing the presence of electrical discharges. In this case, circuitry 211 electrically coupled to contacts 220 via wires 232, acts as a transmitter, transmitting neuron activity (neuron discharge) signals which provide information as to the time and location of neuron discharges, and unit 404 acts as a receiver, receiving and demodulating/decoding these neuron activity signals.

Application of a voltage to contacts 220 near first end 206a results in stimulating low (or high—to be determined by questioning the patient) tones in auditory cortex 150 (see FIGS. 1A and 1B), whereas application of a voltage to contacts 220 near second end 206b results in stimulation of high (or low) tones in auditory cortex 150.

The Intrel II system by Medtronics is one example of a wireless system which can transmit and receive signals between a processor and a multi-programmable neurological pulse generator which can be modified (see discussion below) and used as processor 410 and unit 404. In particular, the pulse generator would be modified into the shape of prosthetic 200 with electrical contacts 220 (not limited to the number of contacts in the Intrel II system) and be lighter and smaller than that of the pulse generator of Intrel II. The processor of Intrel II allows control of the amplitude, duration, repetition rates, etc . . . , of stimulating signals (referred to as pulses).

FIG. 2C shows microchip circuitry 211 embedded in prosthetic 200. Microchip circuitry 211 shown can include a transmitting/receiving antenna 255 which transmits the above discussed neuron discharge signals to transmitter/receiver 404 as well as receives the above discussed processor signals. Microchip circuitry can be near first end 206a but could be imbedded near second end 206b as well. However, it is preferable to have circuitry 211 near first end 206a, because the latter is nearest skull 116—thereby providing a better coupling between it and transmitter/receiver 404.

Figure 2D:
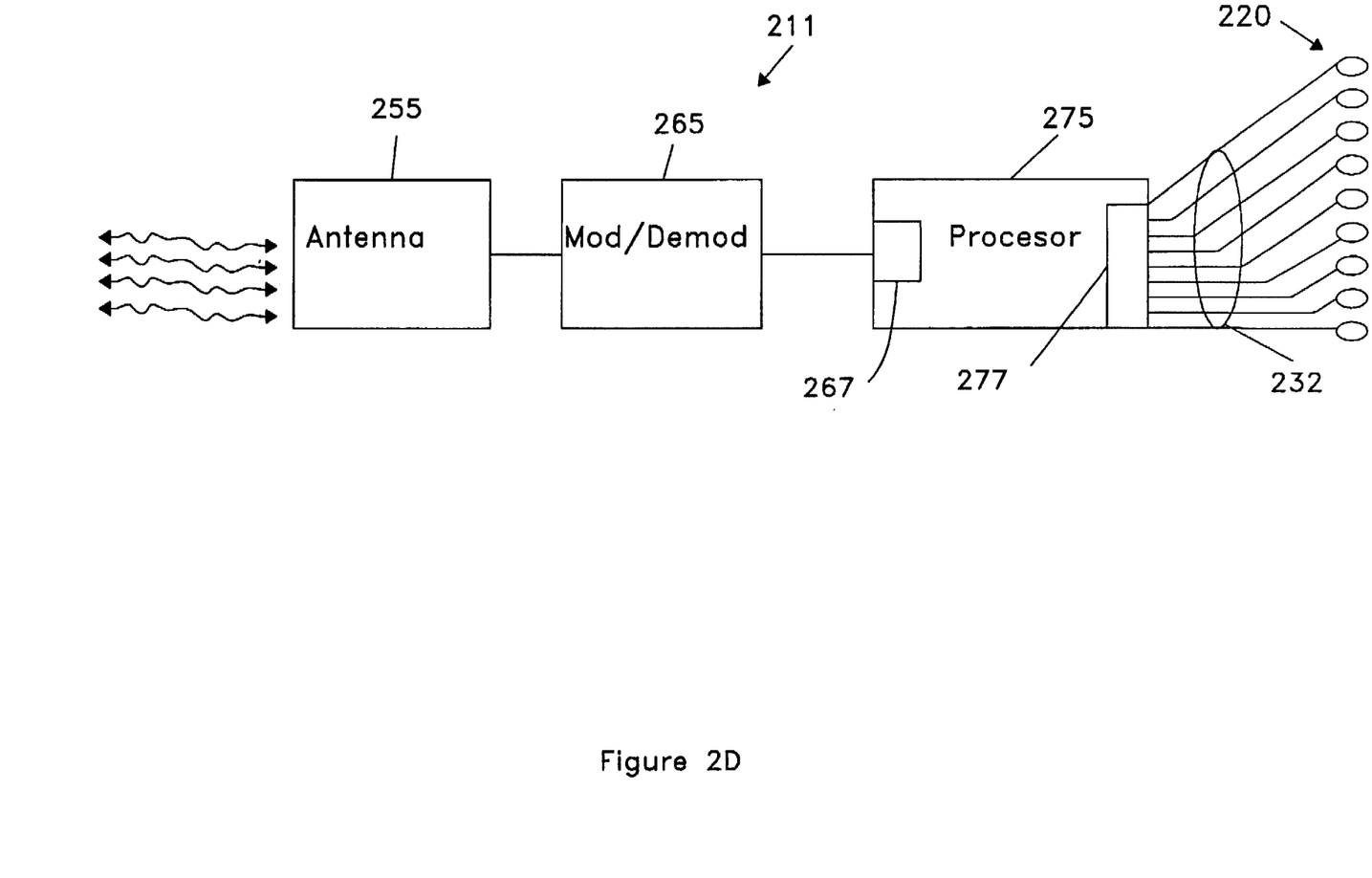
FIG. 2D shows a schematic block diagram of microchip circuitry contained in the wireless prosthetic support.

FIG. 2D shows a schematic block diagram of circuitry 211. In particular, FIG. 2D shows antenna 255 electrically coupled to processor signal modulator/demodulator 265 which in turn is electrically coupled to processor 275. Antenna 255 receives processor signals which can be modulated on an electromagnetic wave carrier which can pass through a patient's skull with little to no damage to the patient. The frequency of the electromagnetic wave carrier can be any frequency which provides the best link between transmitter/receiver 404. Antenna 255 transmits the electromagnetic waves to modulator/demodulator 265 which demodulates these waves and in turn outputs intermediate processor signals to processor 275. Processor 275 can include an analog-to-digital converter 267 which receives and digitizes the intermediate processor signals to yield digital information. Processor 275 processes this digital information and outputs resulting processed information to driver/receiver 277 which is coupled to contacts 222 via wires 232. Driver/receiver 277 in turn stimulates the contacts 220 in accordance with the processed information.

Support 226 can be an active (having on-chip electronics 211) version of any one of the probes shown in FIGS. 3–5 in "Possible Multichannel Recording and Stimulating Electrode Arrays: A Catalog of Available Designs" by the Center for Integrated Sensors and Circuits, University of Michigan Ann Arbor, Michigan, the contents of which are incorporated herein by reference. The on-chip electronics alternative electrodes such as Depthalon Depth Electrodes and interconnection cables from PMT Corporation 1500 Park Road, Chanhassen, Minn., 55317 could also be used as support or electrode 226. Another such on-chip version is the Itrel II system discussed above.

Electrical contacts 220 must operate as high impedance (megohms) contacts or low impedance (a few ohms to several thousand ohms) contacts. High impedance contacts enable the contacts to output a small (a few microamperes as opposed to a few milliamperes) current, which helps localize the potentials applied to the patient's primary auditory cortex to approximately a few hundred micrometers. The localization of applied electric charges corresponds to the tonotopic spacing of nerve cell pairs.

Prosthetic 200 is arranged along a longitudinal direction of auditory cortex 150. However, auditory cortex 150 is located in the transverse temporal gyrus and is buried deep within the Sylvian fissure. Consequently, its location cannot be determined simply by looking at an exposed surface of the brain. Therefore, MRI imaging techniques must be employed to reveal the exact orientation of auditory cortex 150.

A single coronal image of an individual's brain cannot reveal the exact orientation of auditory cortex 150. Instead, a series of images must be obtained and a resulting 3-D MRI image constructed. Once such an image is constructed, the digital data making up that image can be transformed to provide a view of the Sylvian fissure. This in turn exposes auditory cortex 150 as a mole-like mound. That is, tissue on top of the digital image can be "peeled off" to expose the sylvian fissure and consequently auditory cortex 150 "pops out" of the image. This process is described in "Three-dimensional In Vivo Mapping of Brain Lesions in Humans", by Hanna Damasio, Md., Randall Frank, the contents of which are incorporated herein by reference.

Figure 3A:
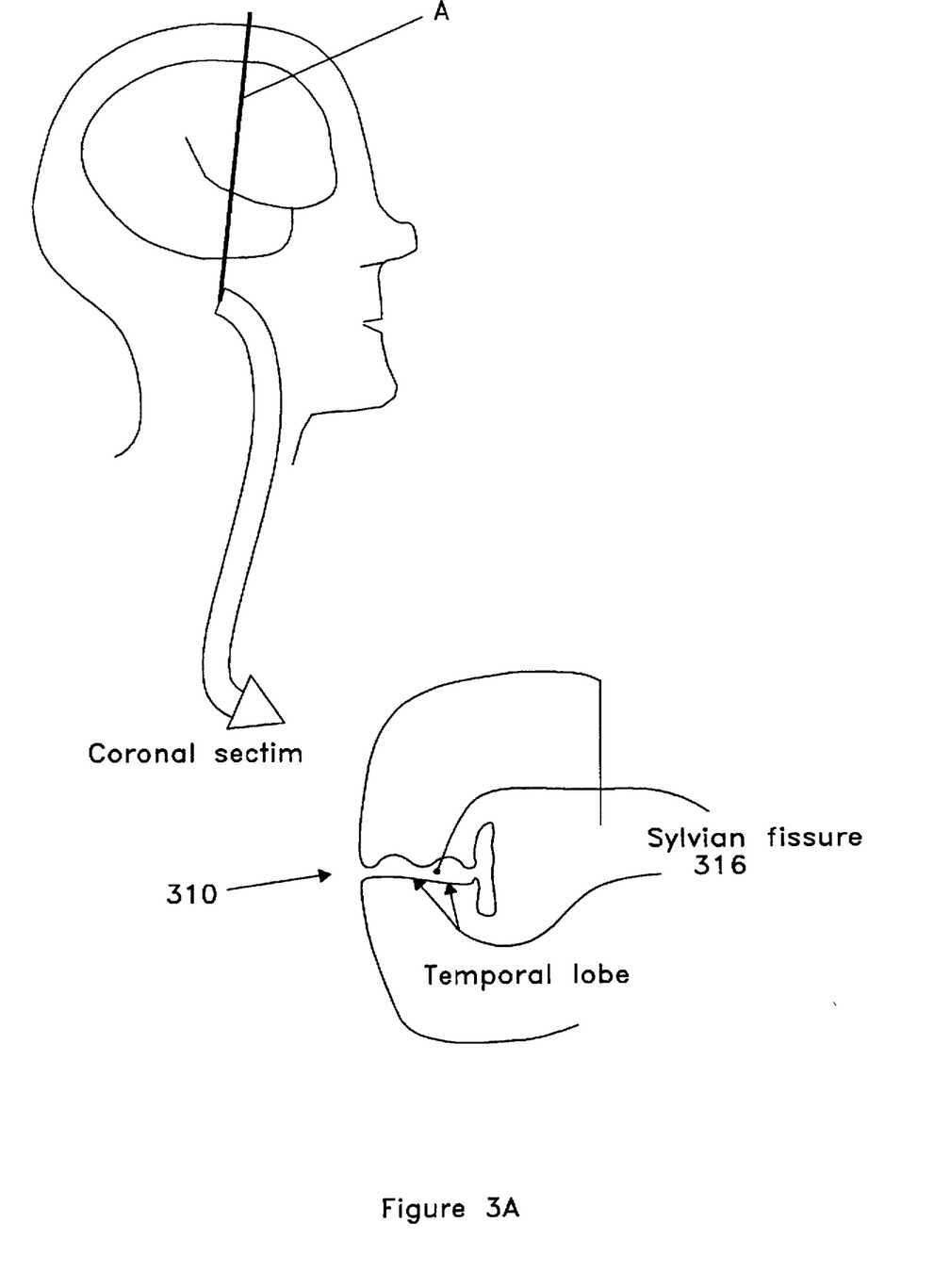
FIG. 3A shows a side view of a plane A which intersects a coronal section with a Sylvian fissure exposed.
Figure 3B:
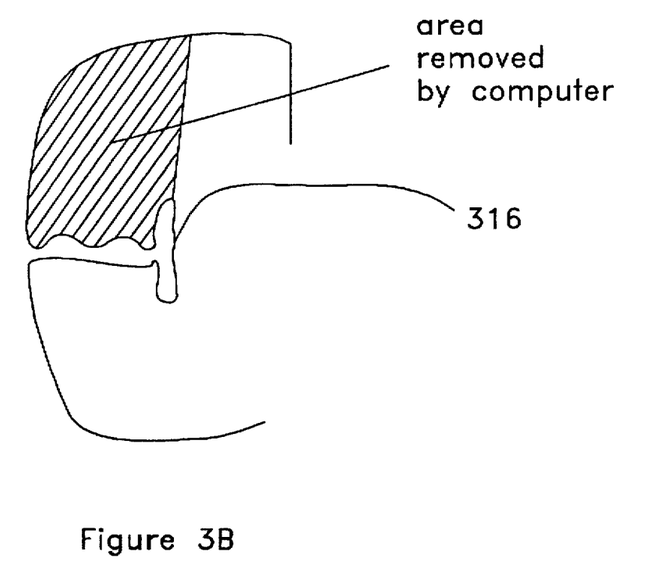
FIGS. 3B and 3C show the coronal section before and after tissue is digitally "peeled off" the Sylvian fissure.
Figure 3C:
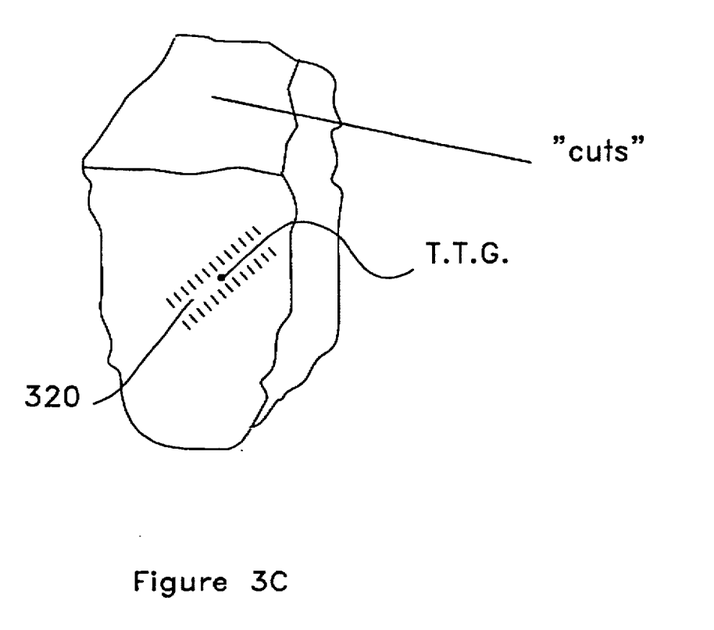

FIG. 3A shows a side view of a plane A which intersects a coronal section 310 as well as a view of coronal section 310 with Sylvian fissure 316 exposed. FIGS. 3B and 3C show coronal section 310 before and after tissue is digitally "peeled off" to expose auditory cortex 150. One or more resulting mounds 320 is revealed in FIG. 3C and this mound corresponds to auditory cortex 150 of FIG. 1B. Mound 320 does not appear until after tissue on the underside of Sylvian fissure 316 is reconstructed to provide the 3-D image.

Once the exact location and orientation of mound 320 and consequently auditory cortex 150 have been determined using these 3-D MRI image processing techniques, the actual primary auditory cortex 150 can be surgically exposed and prosthetic 200 can be accurately inserted into auditory cortex 150.

The Risk Benefit Ratio of Neural Prosthetic Hearing Device

The clinical usefulness of an auditory neural prosthetic device depends on several variables, most importantly the risk-benefit ratio for a given device. An ideal device effectively restores hearing without risk to the patient's overall health. Salient features of two types of devices are outlined below.

Since auditory cortex 150 is situated in temporal lobe 156, neurosurgeons expose this portion of the brain routinely during a wide range of operations. In the non-dominant temporal lobe, unlike the brainstem, the auditory region is not surrounded by vital structures. If a patient is diagnosed with an infiltrating tumor of the non-dominant auditory cortex, for example, the neurosurgeon can resect this tissue with very little risk of complication.

Another example is temporal lobe surgery for intractable epilepsy. Most patients who undergo this surgery are in good general health but suffer from seizures periodically. Usually, chronic epilepsy is not a life threatening condition, and many patients have seizures for decades during which time they are able to work and raise families.

Since most forms of epilepsy are medically "tolerable," surgical treatment directed at curing epilepsy is only justified when it is highly effective and carriers with it very low risk of morbidity and mortality. A properly selected patient in good general health has a less than one percent chance of developing a significant neurologic complication following an elective non-dominant temporal lobectomy for intractable epilepsy, and a 70 percent chance of being cured of their seizures. In that setting, the risk-benefit ratio is strongly in the patient's favor. An operation designed exclusively to place a stimulating neural prosthetic electrode onto non-dominant auditory cortex could be carried out under local anesthesia and take less than two hours operating time. This procedure would entail even less medical risk than a standard epilepsy resection.

Tinnitus

Electrode 104 is stereotaxically placed into the primary auditory cortex of the patient with tinnitus. This can be done using a standard stereotaxic head frame under local anesthesia. That is, the above discussed three dimensional computerized MRI reconstruction method of FIGS. 3A-3C is used to stereotaxically place electrode 104 within the targeted region of auditory cortex 150. Correct placement is confirmed by presenting a series of tones to the patient and mapping the tonotopic responses of the neurons along electrode 104.

In deaf patients, this mapping procedure is not possible, but mapping can still be carried out using microstimulation currents delivered to various contacts along electrode 104. The deaf patient describes the relative pitch of the sounds he or she perceives following stimulation, whereby the electrically stimulated location and parameters which most closely match the patient's tinnitus are determined. This approach could be used in the thalamus (MGN) as well, but the preferred embodiment involves implantation in the cortex. Regardless of whether or not stimulating electrode 104 is placed into the correct region of the cortex or into the correct region of the MGN, electrode 104 is coupled to stimulation device 410 via cables 108 and in particular, wires 232a.

Figure 4A:
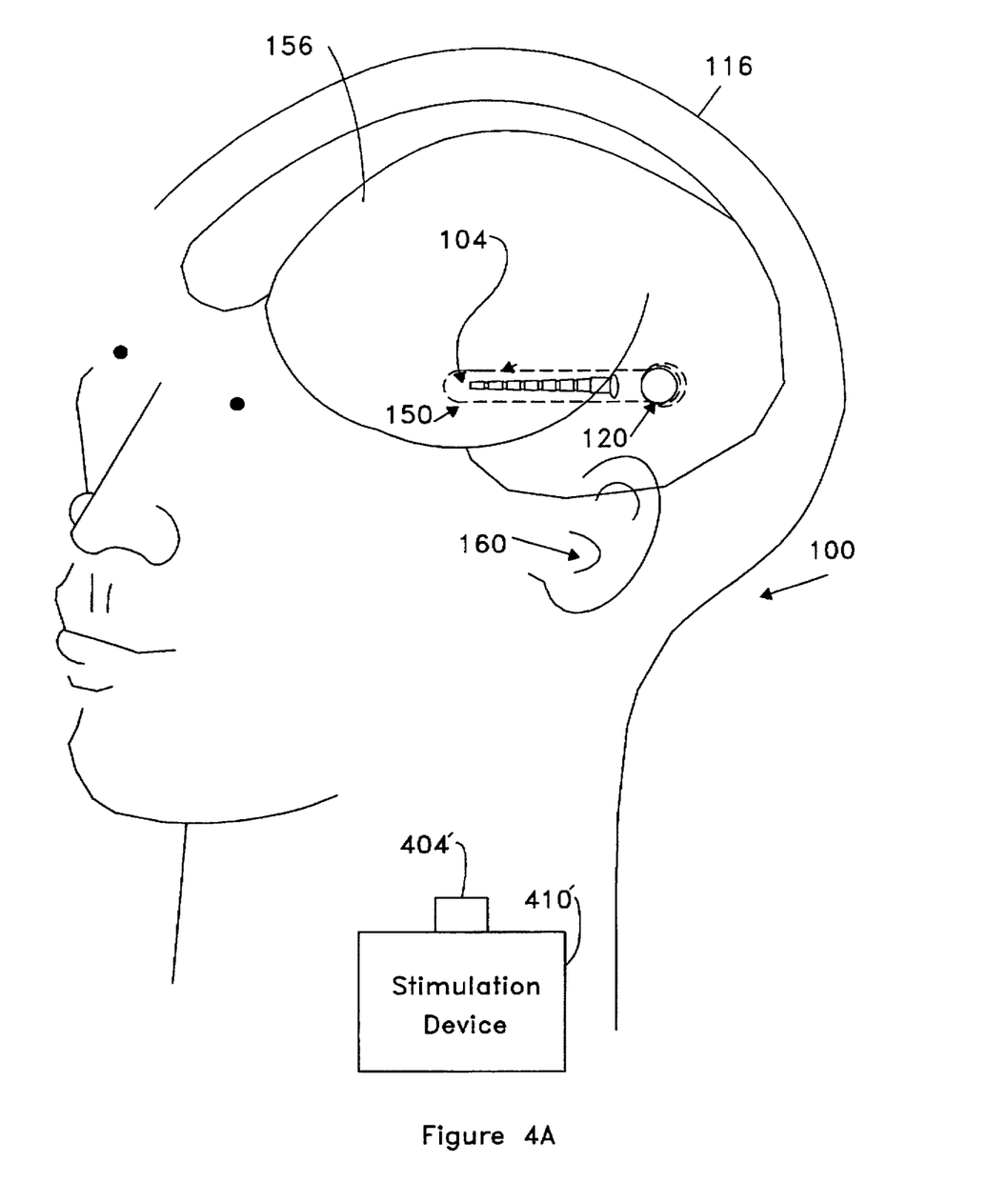
FIG. 4A shows a multi-contact wireless recording/stimulating electrode system 100 for blocking the abnormal electrical activity present in tinnitus patients according to one embodiment of the invention.

Longitudinal support 226 can be a rigid support or a flexible wire with a rigid introducer which enables the physician to introduce electrode 104 into a patient's brain and then subsequently remove the rigid introducer thereby exposing electrical contacts 220 to auditory cortex 150. Support 226 can be one of the probes shown in FIGS. 3–5 in "Possible Multichannel Recording and Stimulating Electrode Arrays: A Catalog of Available Designs" by the Center for Integrated Sensors and Circuits, University of Michigan Ann Arbor, Mich., the contents of which are incorporated herein by reference. Alternative electrodes such as Depthalon Depth Electrodes and interconnection cables from PMT Corporation 1500 Park Road, Chanhassen, Minn., 55317 could also be used as support 226 and electrical couplers between contacts 220 and a stimulation device (410 in FIG. 4).

Electrical contacts 220 must operate as high impedance (megohms) contacts as opposed to low impedance (a few ohms to several thousand ohms) contacts. This enables the contacts to output a small (a few microamperes as opposed to a few milliamperes) current. This also localizes the potentials applied to the patient's primary auditory cortex to approximately a few hundred micrometers. The localization of applied electric charges corresponds to the tonotopic spacing of nerve cell pairs.

Electrode 104 is arranged along a longitudinal direction of auditory cortex 150. However, auditory cortex 150 is located in the transverse temporal gyrus and is buried deep within the Sylvian fissure. Consequently, its location cannot be determined simply by looking at an exposed surface of the brain. Therefore, MRI imaging techniques must be employed to reveal the exact orientation of auditory cortex 150.

A single coronal image of an individual's brain cannot reveal the exact orientation of auditory cortex 150. Instead, a series of images must be obtained and a resulting 3-D MRI image constructed. Once such an image is constructed, the digital data making up that image can be transformed to provide a view of the Sylvian fissure. This in turn exposes auditory cortex 150 as a mound-like mole. That is, tissue on top of the digital image can be "peeled off" to expose the sylvian fissure and consequently auditory cortex 150 "pops out" of the image. This process is described in "Three-dimensional In Vivo Mapping of Brain Lesions in Humans", by Hanna Damasio, Md., Randall Frank, the contents of which are incorporated herein by reference.

FIG. 3A shows a side view of a plane A which intersects a coronal section 310 as well as a view of coronal section 310 with Sylvian fissure 316 exposed. FIGS. 3B and 3C show coronal section 310 before and after tissue is digitally "peeled off" to expose auditory cortex 150. One or more resulting mounds 320 is revealed in FIG. 3C and this mound corresponds to auditory cortex 150 of FIG. 1B. Mound 320 does not appear until after tissue on the underside of Sylvian fissure 316 is reconstructed to provide the 3-D image. Once the exact location and orientation of mound 320 and consequently auditory cortex 150 have been determined using these 3-D MRI image processing techniques, electrode 104 can be accurately inserted into auditory cortex 150.

Stimulating Electrode

FIG. 4A shows a multi-contact recording/stimulating electrode system 100 for blocking and/or masking the abnormal electrical activity present in tinnitus patients according to one embodiment of the invention. In particular, system 100 includes a multi-contact stimulating/recording electrode 104 connected to cables 108 via connector 112. Cables 108 enter skull 116 at burr hole opening 120 of skull 116 and are connected to a stimulation device 410' positioned in subcutaneous tissue of axial skeleton (thorax or abdomen).

Figure 4B:
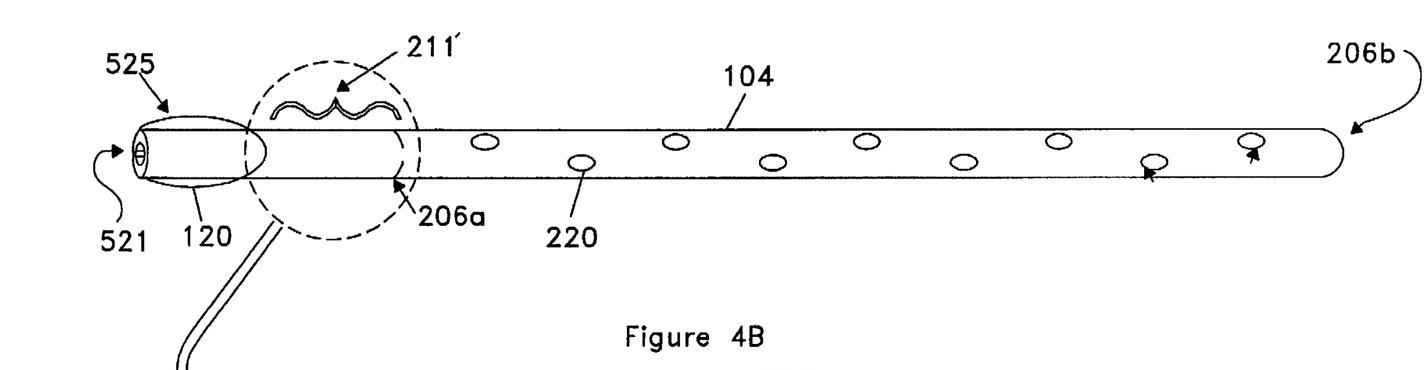
FIG. 4B shows a wireless human cerebral cortex neural prosthetic according to that embodiment of the invention.
Figure 4C:
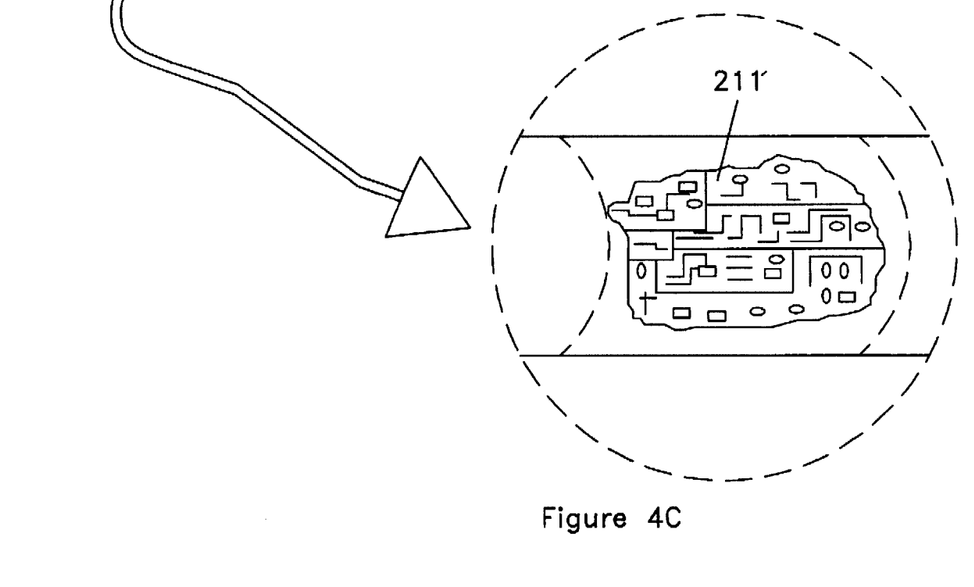
FIG. 4C shows a closeup of the transmission and receiving electronics in the electrode.

FIG. 4B shows a closer view of multi-contact stimulating/recording electrode 104 of electrode system 100. Electrode 104 has a first end 206a and a second end 206b which is blunt or smoothly curved. Electrode 104 has electrical contacts 220 along a longitudinal support 226. Support 226 can be anywhere from several millimeters long to several centimeters long. Electrical contacts 220 are small metal pads which can be separately electrically charged via respective wires 232 available at first end 206a. Wires 232 are coupled to stimulation device 410' (see FIG. 4A). Electrical contacts 220 are spaced approximately 10 micrometers to several millimeters apart and preferably approximately 50 to 150 micrometers apart. Application of a voltage to contacts 220 near first end 206a results in stimulating low (or high—to be determined by questioning the patient) tones in auditory cortex 150 (see FIGS. 1A and 1B), whereas application of a voltage to contacts 220 near second end 206b results in stimulation of high (or low) tones in auditory cortex 150.

Electrode 104 is stereotaxically placed into the primary auditory cortex of the patient with tinnitus. This can be done using a standard stereotaxic head frame under local anesthesia. Alternatively, the above discussed three dimensional computerized MRI reconstruction method of FIGS. 3A–3C can be used to stereotaxically place electrode 104 within the targeted region of auditory cortex 150. Correct placement is confirmed by presenting a series of tones to the patient and mapping the tonotopic responses of the neurons along electrode 104.

In deaf patients, this mapping procedure is not possible, but mapping can still be carried out using microstimulation currents delivered to various contacts along electrode 104. The deaf patient describes the relative pitch of the sounds he or she perceives following stimulation, whereby the electrically stimulated location and parameters which most closely match the patient's tinnitus are determined. This approach could be used in the thalamus (MGN) as well, but the preferred embodiment involves implantation in the cortex. Regardless of whether or not stimulating electrode 104 is placed into the correct region of the cortex or into the correct region of the MGN, electrode 104 is coupled to stimulation device 410' via cables 108 and in particular, wires 232a.

Stimulation device 410 can be a chronic electrical stimulation device. This stimulator device is well tested and widely available. Examples include chronic epidural stimulators made by Medtronics used for chronic back and leg pain, as well as nearly all types of cochlear implants.

Figure 5:
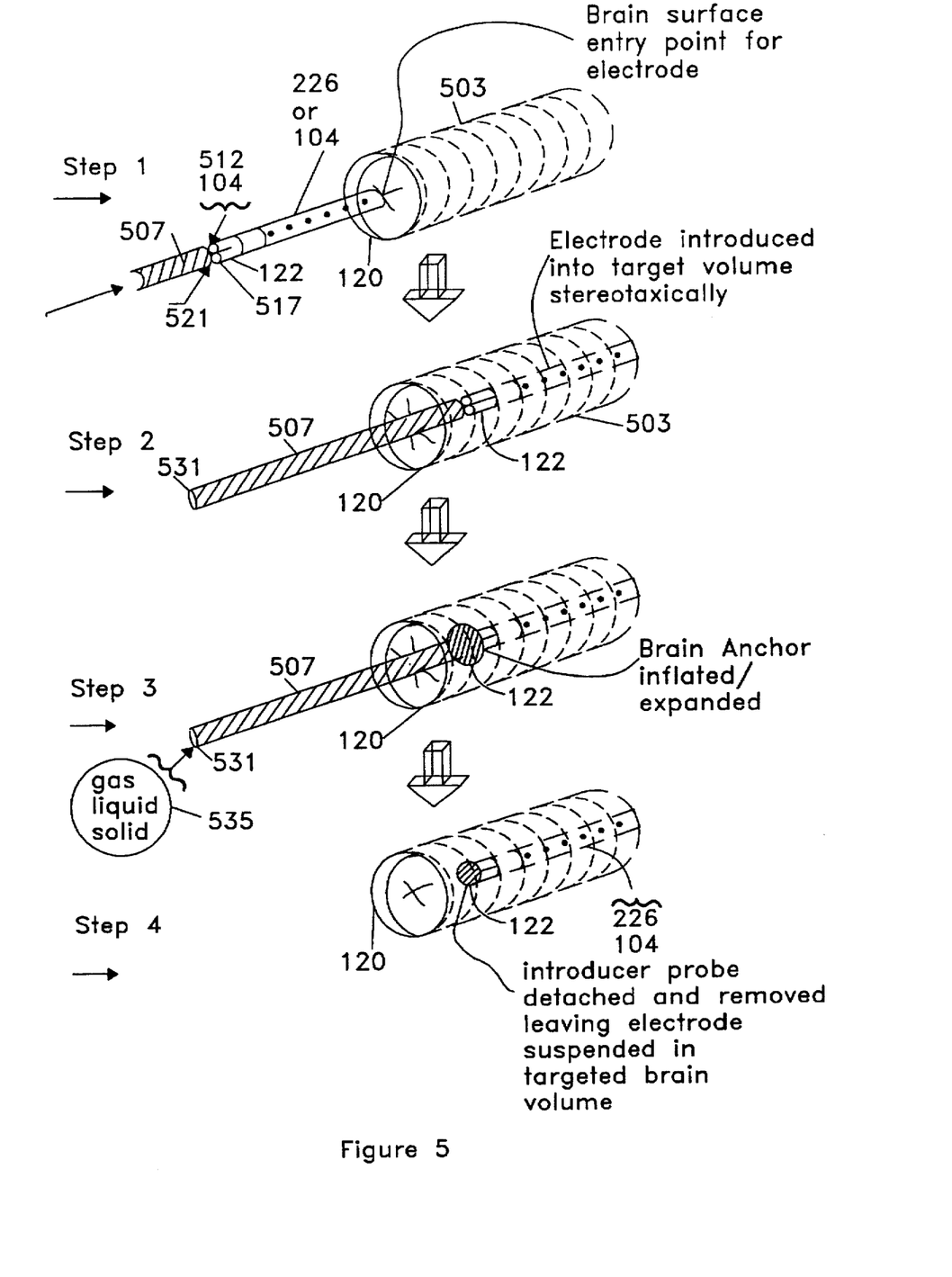
FIG. 5 shows the steps involved in implanting the wireless electrodes (or supports).

FIG. 5 shows how support 226 or electrode 104 are implanted into the patient's brain target zone 503 (auditory cortex or thalamus). As discussed above, brain target zone 503 is determined using stereotaxic techniques as discussed above with respect to FIGS. 3A–3C. Once target zone 503 is determined, step 1 involves attaching a stereotaxic introducer probe 507 onto attachment end 517 which has a female coupler valve 521 (see also FIGS. 2B and 4B). Probe 507 is a standard stereotaxic introducer probe. In particular, the step 1 of attaching probe 507 onto attachment end 517, involves inserting an insertion tip 525 into female coupler valve 521 contained within a deflated or unexpanded brain anchor 122. Brain anchor 122 can be rubber, plastic, or any material which does not cause the patient any adverse complications. Step 2 then involves inserting support 226 or electrode 104 into brain target zone 503. Step 3 involves inflating brain anchor 122 by inputting a gas, liquid or malleable solid material 535 into a back end 531 of probe 507. Finally, once step 3 is complete and anchor 122 is inflated or expanded, step 4 involves detaching probe 507 from attachment end 517 of support 226 or electrode 104 and filling burr hole 120. Prior to detachment, however, the doctor may conduct a series of questions, as discussed above, of the patient and intermittently adjust the orientation of support 226 or electrode 104 for the optimal effect. These questions are different depending on whether support 226 is being inserted into target zone 503 of a hard-of-hearing patient or electrode 104 is being inserted into target zone 503 of a tinnitus patient. The former questioning process is conducted in a manner described above with respect to support 226. The latter questioning process involves repeatedly adjusting the position of electrode 104 using probe 507 and asking the patient if the effects of the tinnitus is improved or worsened, until the optimal orientation is determined.

The above implantation technique for the neural prosthetic for hearing and for tinnitus is quick and safe, e.g., over 100 auditory cortex region electrode implantations have been performed in patients being evaluated for medically intractable seizures. Regarding implantation for tinnitus, since electrode 104 is placed in the exact site of presumed abnormal neuronal electrical activity, it is extremely effective in disrupting or altering abnormal neuronal electrical activity, thereby eliminating tinnitus. Moreover, preliminary testing has shown that placement of electrode 104 within the central auditory system causes patients to perceive sounds and this will be the case for patients who are deaf from causes refractory to cochlear implantation. Also, stimulation in the auditory cortex does not impair hearing in tinnitus patients who do have good hearing.

Figure 6:
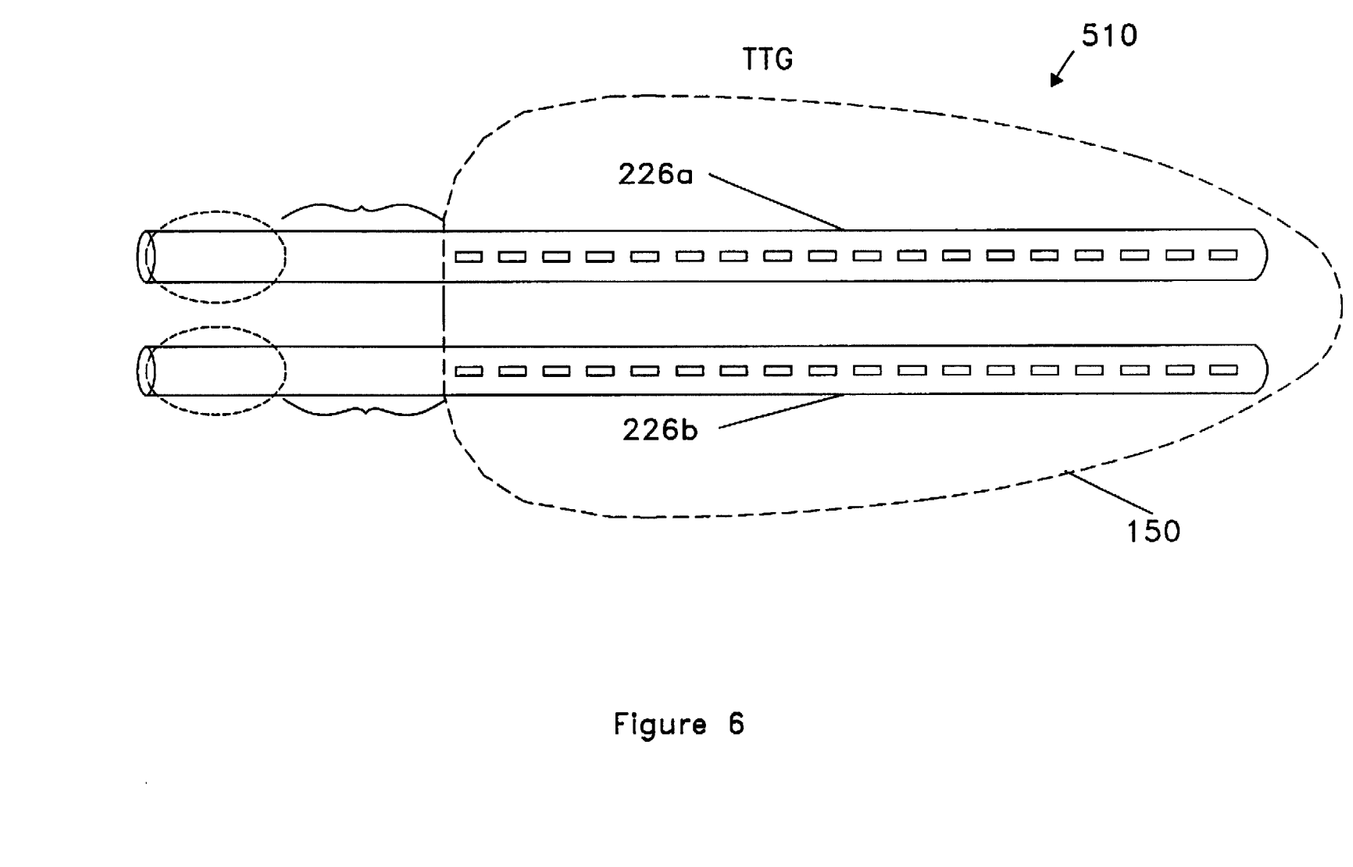
FIG. 6 shows a prosthetic which includes two longitudinal supports for either a human cerebral cortex neural prosthetic system or a multi-contact recording/stimulating electrode system.

FIG. 6 shows an electrode system 510 which includes two longitudinal supports (electrodes) 226a and 226b, according to another embodiment of the invention. Here, supports can correspond to support 226 in FIG. 2B or to multi-contact stimulating and recording electrode 104 in FIG. 4A depending or whether system 510 is for a hard-of-hearing patient or a tinnitus patient, respectively—reference numbers corresponding to the latter will be included in parentheses below. Although two supports are shown, three or more such supports could be used. Longitudinal support 226a is coupled via transmitter/receiver 404 (404' for a tinnitus patient) to speech processor 410 (stimulation device 410') in the same manner that support 226 (multi-contact electrode 104) was coupled to speech processor 410 (stimulation device 410'), namely via a transmitter/receiver link 404 (404').

Numerous additional modifications and variations of the present invention are possible in light of the above teachings. It is therefore understood that the invention may be practiced otherwise than as specifically claimed.

What is claimed is:

1. A wireless neural prosthetic device for placement in a brain target zone of a patient, for receiving processed electrical signals from an exterior processing device, said prosthetic device comprising:

a thin, elongated electrode support adapted for tonotopic arrangement in said brain target zone having a plurality of electrical contacts arranged to electrically couple with said brain target zone; and circuitry electrically coupled to said plurality of electrical contacts for receiving said processed electrical signals and for selectively outputting electrical discharges to said plurality of electrical contacts in accordance with said processed electrical signals.

2. The wireless neural prosthetic device as claimed in claim 1, wherein said plurality of electrical contacts comprise a plurality of metal pads arranged on said electrode support as a three-dimensional array, and wherein said plurality of electrical contacts are adapted for geometric arrangement within said brain target zone.

3. The wireless neural prosthetic device as claimed in claim 1, wherein said electrode support is substantially cylindrical, and wherein said plurality of contacts are electrically coupled to said circuitry by a respective plurality of conductive media.

4. The wireless neural prosthetic device as claimed in claim 1, wherein said plurality of electrical contacts are spaced less than about 2 millimeters apart, and said circuitry is at least partially contained within said electrode support.

5. The wireless neural prosthetic device as claimed in claim 1, wherein said electrode support has an attachment end and a penetrating end, wherein said penetrating end is adapted to penetrate brain tissue to arrive at said brain target zone, and wherein said circuitry is arranged approximately at said attachment end.

6. The wireless neural prosthetic device as claimed in claim 1, further comprising a brain anchor attached to said electrode support for allowing said electrode support to remain within said brain target zone despite brain pulsing.

7. The wireless neural prosthetic device as claimed in claim 6, wherein said brain anchor comprises an inflatable brain anchor.

8. The wireless neural prosthetic device as claimed in claim 6, wherein said brain anchor comprises at least one of rubber and plastic.

9. The apparatus as claimed in claim 1, wherein said circuitry comprises a receiving antenna for receiving said processed electrical signals.

10. The apparatus as claimed in claim 1, further comprising a transmitting antenna coupled to said circuitry, wherein said circuitry receives neural activity signals from said plurality of electrical contacts and transforms said neural activity signals into electromagnetic waves with said neural activity signals modulated thereon and said transmitting antenna transmits said electromagnetic waves.

11. A wireless neural prosthetic system for a targeted brain zone of a patient, comprising:

a processor for outputting processed electrical signals;

a thin, elongate electrode support adapted for tonotopic arrangement in said targeted brain zone and having a plurality of electrical contacts capable of outputting electrical discharges in accordance with said processed electrical signals; and circuitry, electrically coupled to said plurality of electrical contacts, for receiving said processed electrical signals and outputting electrical discharges to said plurality of electrical contacts in accordance with said processed electrical signals.

12. The apparatus as claimed in claim 11, further comprising a transmitting antenna coupled to said circuitry, wherein said circuitry receives neural activity signals from said plurality of electrical contacts and transforms said neural activity signals into electromagnetic waves with said neural activity signals modulated thereon and said transmitting antenna transmits said electromagnetic waves.

13. The apparatus as claimed in claim 12, further comprising a processor antenna coupled to said processor for receiving and transmitting said electromagnetic waves to said processor.

14. The apparatus as claimed in claim 13, wherein said processor demodulates said electromagnetic waves, thereby yielding signals corresponding to said neural activity.

15. A neural prosthetic apparatus for an auditory cortex of a patient, comprising:

- a speech processor for receiving and processing audio information and for outputting processed electrical signals;
- a thin, elongated electrode support adapted for tonotopic arrangement in said auditory cortex and having a plurality of electrical contacts arranged on said electrode support, wherein each of said plurality of electrical contacts is adapted to output electrical discharges in accordance with said processed electrical signals; and
- circuitry electrically coupled to said plurality of electrical contacts for receiving said processed electrical signals and outputting electrical discharges to said plurality of electrical contacts in accordance with said processed electrical signals.

16. The neural prosthetic apparatus as claimed in claim 15, wherein said electrode support is adapted for stereotactic placement in said auditory cortex of the patient, and said plurality of electrical contacts are arranged on said electrode support such that each of said plurality of electrical contacts is capable of stimulating a geometrically separate location of said auditory cortex.

17. The neural prosthetic apparatus as claimed in claim 16, further comprising:

- at least one additional electrode support adapted for tonotopic arrangement in said auditory cortex, said at least one additional electrode support having an additional plurality of electrical contacts, said additional plurality of electrical contacts being capable of outputting additional electrical discharges in accordance with said electrical signals.

18. The neural prosthetic apparatus as claimed in claim 15, wherein said plurality of electrical contacts are approximately uniformly arranged along said electrode support.

19. The neural prosthetic apparatus as claimed in claim 15, wherein said electrical contacts are spaced approximately 50 to 150 micrometers apart.

20. A neural prosthetic apparatus for an auditory cortex of a patient, comprising:

- a speech processor for receiving and processing audio information and for outputting processed electrical signals;
- a thin, elongated electrode support adapted for tonotopic arrangement within said auditory cortex and having a plurality of electrical contacts approximately uniformly arranged along said electrode support, each of said plurality of electrical contacts being capable of independently outputting electrical discharges in accordance with said processed electrical signals; and
- circuitry electrically coupled to said plurality of electrical contacts for receiving said processed electrical signals and outputting electrical discharges to said plurality of electrical contacts in accordance with said processed electrical signals.

21. A neural prosthetic apparatus for a patient with tinnitus, comprising:

- a stimulation device for outputting electrical signals; and
- a thin elongated electrode support, adapted for arrangement in the patient's cortex or thalamus, said electrode support having a plurality of electrical contacts electrically coupled to said stimulation device, said plurality of electrical contacts capable of selectively outputting electrical discharges in accordance with said electrical signals.

22. The neural prosthetic apparatus as claimed in claim 21, further comprising:

- at least one additional electrode support having an additional plurality of electrical contacts electrically coupled to said stimulation device, said at least one additional electrode support being adapted for tonotopic arrangement in the patient's cortex or thalamus, said additional plurality of electrical contacts being capable of outputting additional electrical discharges in accordance with said electrical signals.

* * * * *